(12) United States Patent
Vandecar et al.

(10) Patent No.: US 10,314,874 B2
(45) Date of Patent: Jun. 11, 2019

(54) PLANT AND ANIMAL EXTRACTS AND RELATED METHODS

(71) Applicants: Christopher Vandecar, Thousand Oaks, CA (US); Dana Vandecar, Thousand Oaks, CA (US)

(72) Inventors: Christopher Vandecar, Thousand Oaks, CA (US); Dana Vandecar, Thousand Oaks, CA (US)

(*) Notice: Subject to any disclaimer, the term of this patent is extended or adjusted under 35 U.S.C. 154(b) by 543 days.

(21) Appl. No.: 14/682,008

(22) Filed: Apr. 8, 2015

(65) Prior Publication Data

US 2016/0008417 A1   Jan. 14, 2016

Related U.S. Application Data

(60) Provisional application No. 61/976,931, filed on Apr. 8, 2014, provisional application No. 61/976,945, filed on Apr. 8, 2014.

(51) Int. Cl.
| | | |
|---|---|---|
| *A61K 35/10* | (2015.01) | |
| *A61K 36/48* | (2006.01) | |
| *A61K 36/31* | (2006.01) | |
| *A61K 36/736* | (2006.01) | |
| *A61K 35/32* | (2015.01) | |
| *A61K 35/407* | (2015.01) | |
| *A61K 36/185* | (2006.01) | |

(52) U.S. Cl.
CPC ............ *A61K 36/48* (2013.01); *A61K 35/32* (2013.01); *A61K 35/407* (2013.01); *A61K 36/185* (2013.01); *A61K 36/31* (2013.01); *A61K 36/736* (2013.01); *A61K 2236/00* (2013.01)

(58) Field of Classification Search
CPC ..................................................... A61K 35/10
USPC ..................... 424/600, 725.1, 725
See application file for complete search history.

(56) References Cited

U.S. PATENT DOCUMENTS

| | | | |
|---|---|---|---|
| 5,626,881 A | 5/1997 | Lown | |
| 6,440,436 B1 | 8/2002 | Ghosal | |
| 6,558,712 B1 * | 5/2003 | Ghosal | ................ A61K 36/00 424/195.18 |

(Continued)

FOREIGN PATENT DOCUMENTS

| | | | |
|---|---|---|---|
| CN | 103519214 A | * | 1/2014 |
| CN | 103564587 A | * | 2/2014 |

(Continued)

OTHER PUBLICATIONS

Wikipedia website document entitled "Relative density". Downloaded on Oct. 15, 2018 from https://en.wikipedia.org/wiki/Relative_density, 11 pages.*

(Continued)

*Primary Examiner* — Christopher R Tate
(74) *Attorney, Agent, or Firm* — Thorpe North & Western LLP

(57) ABSTRACT

The present disclosure is drawn to methods for producing natural extracts utilizing fulvic acid solutions as well as the extracts produced utilizing the disclosed methods. The method provides for selecting natural material(s) for extraction and contacting the natural material with a fulvic acid solution. In some embodiments the contacting can occur by pouring, dripping, sprinkling, submersing, or substantially submersing the natural material with the fulvic acid solution.

22 Claims, 4 Drawing Sheets

(56) References Cited

U.S. PATENT DOCUMENTS

| | | | |
|---|---|---|---|
| 7,896,944 B2 | 3/2011 | Karr | |
| 7,964,234 B2 | 6/2011 | Mower et al. | |
| 8,383,840 B1 | 2/2013 | McMahon | |
| 8,440,241 B1 * | 5/2013 | Grady | A23L 33/15 |
| | | | 424/725 |
| 9,820,953 B2 * | 11/2017 | Black | A61K 35/10 |
| 2003/0039662 A1 | 2/2003 | Ghosal | |
| 2004/0261481 A1 | 12/2004 | Anaya-Olvera | |
| 2007/0212434 A1 * | 9/2007 | Day | A61K 8/498 |
| | | | 424/762 |
| 2009/0204187 A1 * | 8/2009 | Mankovitz | A61K 31/19 |
| | | | 607/88 |
| 2010/0010089 A1 * | 1/2010 | Van Dyke | C05F 11/02 |
| | | | 514/568 |
| 2011/0237438 A1 | 9/2011 | Marihart | |
| 2012/0149697 A1 * | 6/2012 | Legname | A61K 31/194 |
| | | | 514/229.8 |
| 2012/0279266 A1 | 11/2012 | Van Dyke et al. | |
| 2013/0337116 A1 * | 12/2013 | Petralia | A61K 36/886 |
| | | | 426/61 |
| 2017/0246132 A1 * | 8/2017 | Black | A61K 35/10 |

FOREIGN PATENT DOCUMENTS

| | | | |
|---|---|---|---|
| JP | 2006087393 A | * | 4/2006 |
| KR | 100197168 B1 | | 6/1999 |

OTHER PUBLICATIONS

Office Action dated Dec. 4, 2017, in Australian Patent Application No. 2015243531, filed Apr. 8, 2015; 7 pages.

* cited by examiner

PLANT AND ANIMAL EXTRACTS AND RELATED METHODS

PRIORITY CLAIM

This application claims priority to U.S. Provisional Application No. 61/976,931 filed on Apr. 8, 2014 and U.S. Provisional Application No. 61/976,945 filed on Apr. 8, 2014.

BACKGROUND

Natural compositions from plants and animals have long been thought to provide a variety of health benefits. However, the ability of most people to consume the quantities of these materials to achieve the desired benefit is often limited. Accordingly, the extracts of such compositions have been relied upon to try to provide the desired benefits without the consumption of large quantities of the particular natural composition. However, not all extraction methods are capable of adequately extracting all of the desired beneficial components. Many extraction techniques utilize heat or undesirable additives, such as alcohol or acids, which can result in degradation and undesirable loss of beneficial properties, such as nutrients, vitamins, biomarkers, enzymes, minerals or fatty acid components. Additionally, many extraction techniques introduce impurities and other compounds, which may result in the resulting extract having undesirable properties. Accordingly, need exists for a better extraction technique.

SUMMARY OF THE INVENTION

The present disclosure is drawn to methods for producing natural extracts utilizing a fulvic acid solution as well as the extracts produced utilizing the disclosed methods. The method provides for selecting natural material(s) for extraction and contacting the natural material with a fulvic acid solution. In some embodiments the contacting can occur by pouring on, dripping on, sprinkling on, submersing in, or substantially submersing the natural material in the fulvic acid solution.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
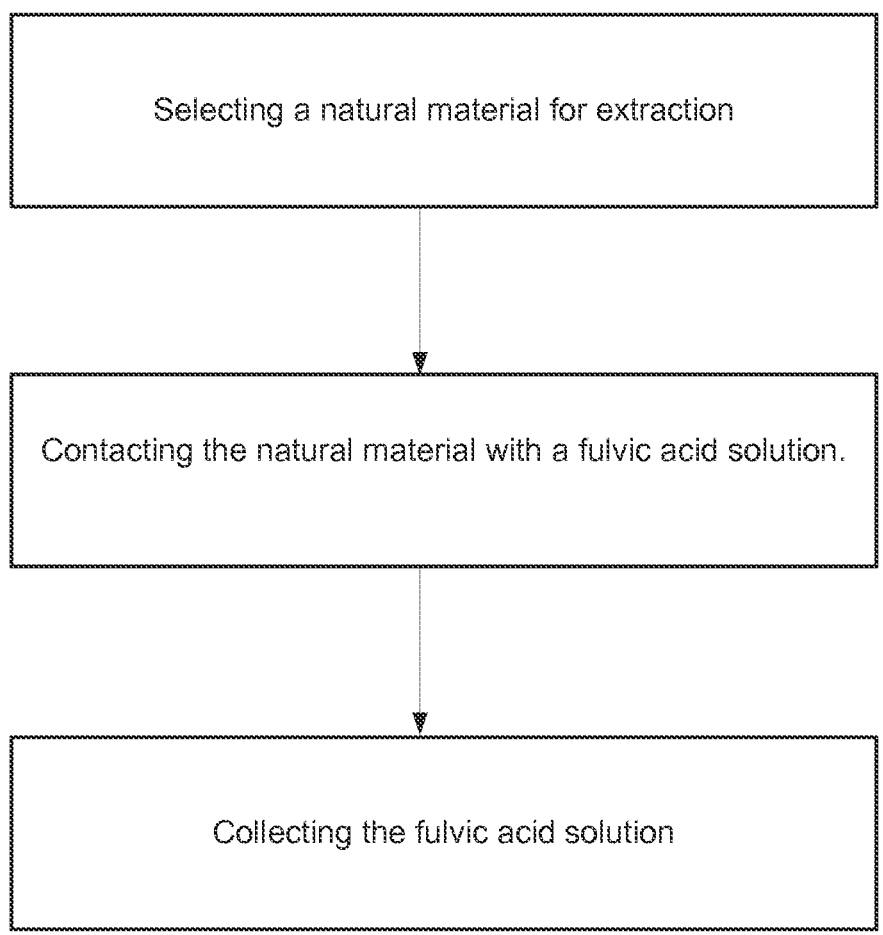
FIG. 1 is a flow diagram of a general method of producing an extract of a natural material in accordance to an embodiment of the present disclosure.
Figure 2:
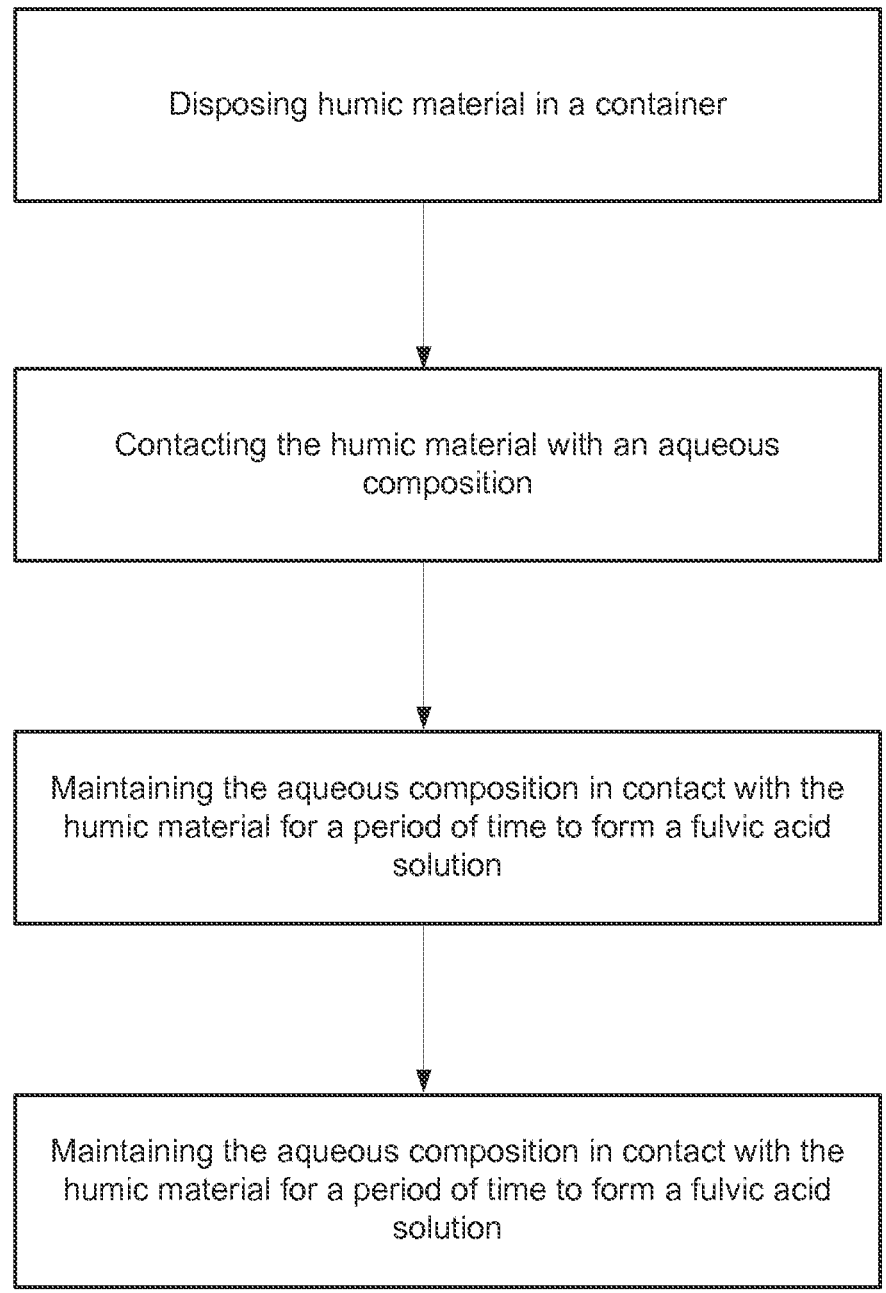
FIG. 2 is a flow diagram of a general method for producing a fulvic acid solution that can be used in embodiments of the methods disclosed herein.
Figure 3:
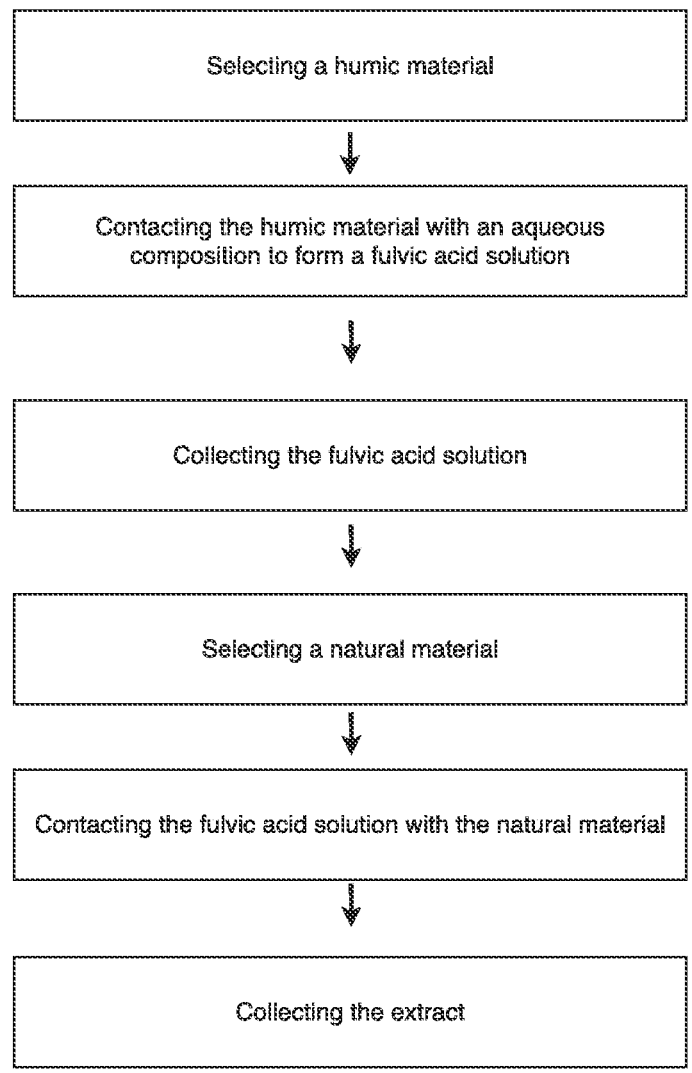
FIG. 3 is a flow diagram of a general method of producing an extract of a natural material in accordance to an embodiment of the present disclosure.
Figure 4:
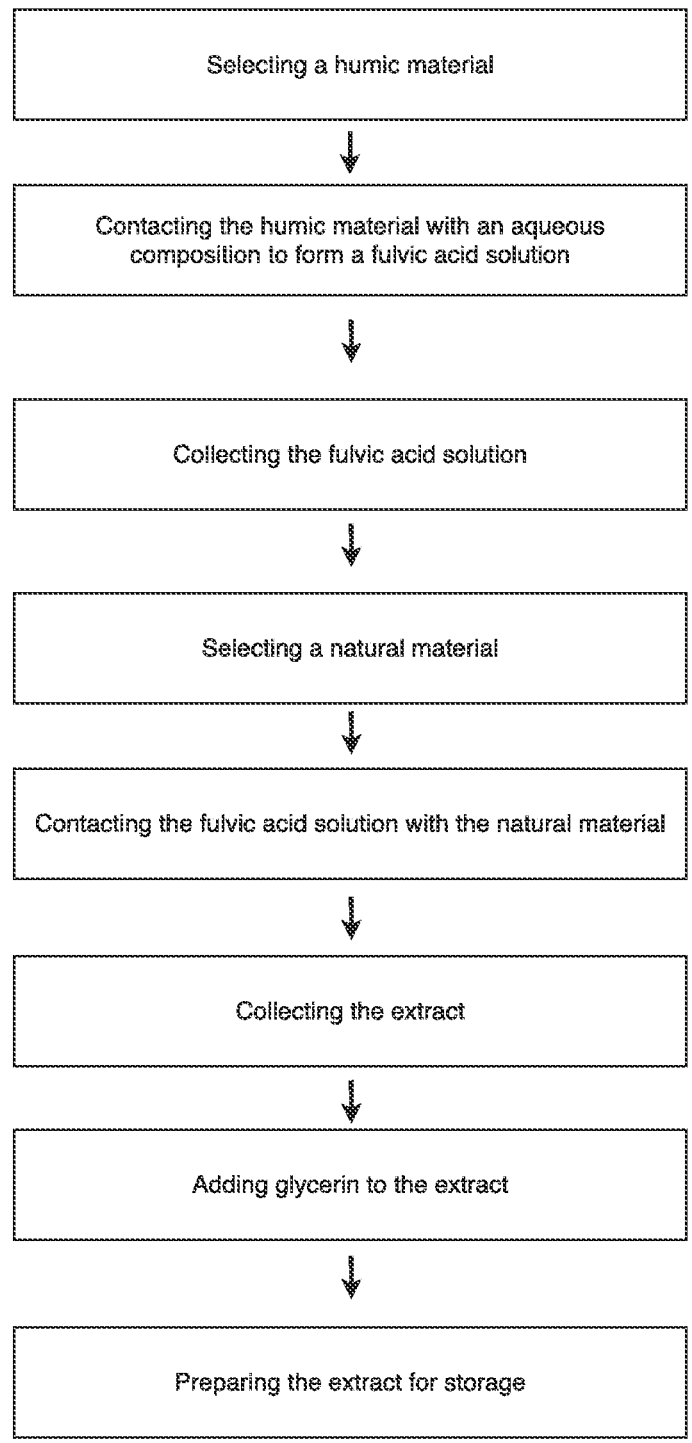
FIG. 4 is a flow diagram of a general method of producing an extract of a natural material in accordance to an embodiment of the present disclosure.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

In describing embodiments of the present invention, the following terminology will be used.

The singular forms "a," "an," and "the" include plural referents unless the context clearly dictates otherwise. Thus, for example, reference to "an extract" includes reference to one or more of such extracts. "Extract" may also refer to solutions comprising combinations of fulvic acid and one or more extracts.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art. Further, unless otherwise stated, the term "about" shall expressly include "exactly," consistent with the discussion above regarding ranges and numerical data.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the "fulvic acid" can refer to compositions containing fulvic acids and/or humic acids and/or trace minerals and combinations thereof. Thus, a fulvic acid solution can include fulvic acids alone, humic acids alone, or a mixture or combination of both fulvic acids and humic acids, fulvic acids in combination with trace minerals, humic acids combined with trace minerals, or combinations of fulvic acids, humic acids, and trace minerals.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 milligrams" should be interpreted to include not only the explicitly recited values of about 50 milligrams and 250 milligrams, but also include individual values and sub-ranges within the indicated range. Thus, included in this numerical range are individual values such as 60, 70, and 80 milligrams, and sub-ranges such as from 50-100 milligrams, from 100-200 milligrams, and from 100-250 milligrams, etc. This same principle applies to ranges reciting only one numerical value and should apply regardless of the breadth of the range or the characteristics being described.

With the above in mind, the present disclosure provides for a method of producing an extract from a natural material. The method includes contacting the natural material with a fulvic acid solution.

The contacting of the natural materials by the fulvic acid solution during the extraction process can occur by pouring, dripping, sprinkling or otherwise contacting the natural materials with the fulvic acid solution to form an extract solution. In one aspect, the extract solution can be collected and repeatedly poured, dripped, or sprinkled over the natural materials in order to further extract the natural materials.

This collection and re-pouring or re-contacting of the extract solution can occur one or more times depending on different variables such as the desired concentration of the extract and the nature of the materials being extracted. In one aspect, the extract solution can be collected and poured or re-poured over the natural materials 2 to 100 times. In another aspect, the extract solution can be collected and poured or re-poured over the natural materials 5 to 50 times. In one aspect of the invention, the method for producing the extract of natural materials can be accomplished without heating, without the addition of additional chemical agents, or without alcohol.

In some aspects, the natural materials can be submerged or substantially submerged into the fulvic acid solution to product an extract solution. In one aspect, the natural material can be completely submerged in the fulvic acid solution. The duration of the submersion can be for a period of 30 seconds to 90 days. In one aspect, the natural material can be submersed in the fulvic acid solution for a period of 1 minute to 45 days. In one aspect, the natural material can be submersed in the fulvic acid solution for a period of 1 minute to 30 days. In one aspect, the natural material can be submersed in the fulvic acid solution for a period of 1 minute to 14 days. In still another aspect, the natural material can be submersed in the fulvic acid solution for a period of 5 minutes to 7 days. In still another aspect, the natural material can be submersed in the fulvic acid solution for a period of 5 minutes to 3 days. In one aspect, the natural material can be submersed in the fulvic acid solution for a period of 5 minute to 24 hours. In other aspects, the natural materials can be floated or partially submerged in an aqueous solution and a fulvic acid solution can be poured or sprinkled over the natural materials.

In some aspects of the disclosed method, the natural material and the fulvic acid solution can be mixed, stirred, or otherwise agitated to increase the contacting of the fulvic acid with the natural material. The nature and duration of the agitation can vary depending on the type of material being extracted, the amount of material being extracted, the container in which the extraction is being performed, or combinations of these and other factors. The mixing or agitation can be mild so as to only circulate the fulvic acid solution or it can be aggressive enough to cause movement, and in some cases even some maceration, of the natural material being extracted.

In some aspects of the invention, the method can also include filtering the extract solution. In one aspect, the filtration can be configured to remove all particulates and solid material from the extract solution. In other aspects, the filtration can be designed to leave some small particulates behind. In one aspect, the filtration can utilize a filter designed to remove all particles having diameters of greater than about 10 microns. In another aspect, the filtration can utilize a filter designed to remove all particles having diameters of greater than about 7.5 microns. In another aspect, the filtration can utilize a filter designed to remove all particles having diameters of greater than about 5 microns.

A variety of natural materials can be extracted utilizing the methods disclosed herein. For example, in one aspect the natural material can be a plant material, an animal material, or combinations thereof. The natural material can be extracted in its raw natural form. In some aspects the natural material can be dried, freeze-dried, baked, or otherwise processed into a non-raw form. Further, the natural material can be diced, ground, chopped, or otherwise physically processed to facilitate the extraction process.

Non-limiting examples of plant materials that can be extracted using the disclosed methods include herbs, edible fungi, fruit, flowers, seeds, nuts, vegetables, and combinations thereof. Specific herbs that can be extracted by the method can include, but are not limited by basil, black pepper, chili pepper, cinnamon bark, clove, fennel seed, ginger, hibiscus flower, horseradish, lemon grass, licorice, oregano, parsley, peppermint, rosemary, sage, star anise, thyme, turmeric, white pepper, and combinations thereof.

Non-limiting examples of edible fungi that can be extracted include chaga mushroom, reishi mushroom, shiitake mushroom, maitake mushroom, turkey tail mushroom, oyster mushroom, wood ear mushroom, poria cocos (Fu Lin), *agaricus blazei* (Murrill), king bolete cepe, cordyceps, *grifola umbellata* (Zhu Ling), winter mushroom, beef steak mushroom, matsutake mushroom, true tinder polypore, and combinations thereof.

Non-limiting examples of edible flowers that can be extracted include American elderberry (*Sambucus canadensis*), anise hyssop (*Agastache foeniculum*), arugula (*Eruca sativa*), basil (*Ocimum basilicum*), bean (*Phaseolus vulgaris*), bergamot (*Monarda didyma*), broccoli (*Brassica oleracea* var. italics), cauliflower (*Brassica oleracea*), chamomile (*Chamaemelum nobile*), chervil (*Anthriscus cerefolium*), Chinese hibiscus (*Hibiscus rosa-sinensis*), chives (*Allium schoenoprasum*), chicory (*Cichorium intybus*), chrysanthemum (*Chrysanthemum* spp.), cornflower (*Centaurea cyanus*), dandelion (*Taraxacum officinale*), dianthus (*Dianthus* spp.), dill (*Anethum graveolens*), English marigold (*Calendula officinalis*), English daisy (*Bellis perennis*), fennel (*Foeniculum vulgare*), geranium (*Pelargonium* spp.), hollyhock (*Alcea rosea*), Japanese honeysuckle (*Lonicera japonica*), lavender (*Lavandula* spp.), lilac (*Syringa vulgaris*), lovage (*Levisticum officinale*), mint (*Mentha* spp.), nasturtium (*Tropaeolum majus*), okra (*Abelmoschus esculentus*), passionflower (*Passiflora* spp.), pineapple sage (*Salvia elegans*), red clover (*Trifolium pratense*), rose (*Rosa* spp.), rosemary (*Rosmarinus officinalis*), sage (*Salvia officinalis*), snapdragon (*Antirrhinum majus*), squash (*Cucurbita pepo*), sunflower (*Helianthus annuus*), thyme (*Thymus vulgaris*), tulip (*Tulipa* spp.), violet (*Viola odorata*), and combinations thereof.

Non-limiting examples of fruit that can be extracted include acai berry, acerola cherry, noni fruit, maqui berry, mangosteen, coconut flesh, banana, blackberry, apple, apricot, black currant, blueberry, cherry, cranberry, grape, honeydew melon, lemon, key lime, lime, orange, peach, pomegranate, red raspberry, strawberry, tangerine, euphoria fruit, fig fruit, grapefruit, hawthorne berry, jujube fruit, kiwi, luo han guo, mango, mulberry, papaya, pear, pineapple, plum, watermelon, bilberry, lycii berry, Chinese winter melon, seabuckthorn berry, cupuacu, camu camu, and combinations thereof.

Non-limiting examples of vegetables that can be extracted include vegetables artichoke, asparagus, bamboo, bean sprout, beet, bell pepper, bitter melon, black bean, black rice, broccoli, cabbage, carrot, cauliflower, celery, Chinese yam, cucumber, daikon radish, eggplant, garlic, green bean, green onion, kelp, leek, lettuce, lotus root, onion, pea, pumpkin, radish, red bean, seaweed, soybean, spinach, squash, sweet potato, tomato, water chestnut, wheat grass, barley grass, white kidney bean, kelp, maca root, cacao beans, and combinations thereof. Non-limiting examples of seeds that can be extracted include fonio, maize (corn), pearl millet, oats, palmer's grass, rice, rye, sorghum, spelt, teff, triticale, wheat, wild rice, hemp, flax, chia, quinoa, and combinations thereof. Non-limiting examples of nuts that can be extracted include beech nuts, acorns, breadnut, candlenut, hazelnuts, chestnuts, almond, kola nut, kurrajong, Malabar, palm nuts, karuka, walnut, red bopple nut, cashnew nut, betel, pecans, gabon nut, and combinations thereof.

In another aspect, the natural material for extraction can be an animal material. Non-limiting examples of animal materials that can be extracted utilizing the disclosed methods include antlers, animal muscle (meat), animal organs, and combinations thereof. While the disclosed method can be accomplished at any temperature, for economic purposes it can be useful to perform the method at ambient or room temperature. Excessively cold temperatures can inhibit the extraction process as the solution or the natural material can freeze. Excessively hot temperatures require the expenditure of energy and can degrade the natural material and inhibit its beneficial properties. Typically, the method can also be performed at standard or ambient pressures, although increased or elevated pressures can also be applied.

In some aspects, the fulvic acid extract solution can be supplemented with stabilizers, pH adjusters, or other excipients or agents that can be added to enhance the storage stability, taste, or other characteristic of the extract. Non-limiting examples of such agents can include magnesium stearate, citric acid, combinations thereof, and the like. In one aspect, glycerin can be added to the fulvic acid extract solution to stabilize the solution, protect against degradation, and make the fulvic acid extract solution more suitable for storage. In one aspect, the glycerin used is vegetable glycerin.

In some aspects, the extraction methods of the present invention can be accomplished without the use of any additional materials outside the fulvic acid solution and the natural extract. Specifically, in some aspects the disclosed method can be performed without the use of additional microbes, chemicals, minerals, or the like.

The fulvic acid solutions used in the methods of the present invention can generally be any fulvic acid solution having a specific gravity of at least about 1. In a preferred embodiment, the fulvic acid solution can have a specific gravity of at least about 10. In a further embodiment, the fulvic acid solution can have a specific gravity of about 10 to about 100. Non-limiting examples of commercially available fulvic acid solutions that can be used include, but are not limited to, Fulvic Ion Minerals X200 (specific gravity of 50) and Fulvic Ion Minerals X350 (specific gravity of 70) (each sold by Optimally Organic™)

In one aspect of the present disclosure, the fulvic acid solution for use in the claimed method of extraction can be prepared accordingly to a particular method. Specifically, in one aspect, the fulvic acid solution can be prepared by disposing humic material in a container, contacting the humic material with an aqueous composition, maintaining the aqueous composition in contact with the humic material for a period of time to form a fulvic acid solution, and collecting the fulvic acid solution. In one aspect, the step of contacting includes pouring or dripping the aqueous composition over the humic material and allowing it pass through and around the humic material.

The aqueous composition can be maintained in contact with the humic material for a period of time of about 24 hours to about 21 days. In one aspect, the aqueous composition can be maintained in contact with the humic material for a period of time of about 36 hours to about 15 days. In another aspect, the aqueous composition can be maintained in contact with the humic material for a period of time of about 5 days to about 14 days.

The humic material that can be used to make the fulvic acid solution can be selected from a variety of known humic acid materials including, but not limited to, humic shale, lignite, coal, plant material (e.g. sugar cane), and combinations thereof. In one aspect, the humic material can be humic shale. In another aspect, the humic shale can be dried or cured for a period of 1 to 2 years prior to the manufacture of the fulvic acid solution.

The aqueous composition used in the preparation of the fulvic acid solution can be water or other aqueous solution. In one aspect, the water is distilled water. In another aspect, the water has been purified and is free of any chlorine or fluoride. In some aspects, the aqueous composition used in the formation process can be a fulvic acid solution, e.g. one having a lower specific gravity. In such embodiments, the method of preparing the fulvic acid solution can include the step of contacting the humic material with the fulvic acid solution. The contacting of the humic material with the fulvic acid solution can result in a fulvic acid solution with a higher specific gravity relative to the fulvic acid solution that contacted the humic material.

The method of producing the fulvic acid solution can further include adding distilled water to the fulvic acid solution to adjust the specific gravity of the fulvic acid solution. In another embodiment, the method can further include adding a pH adjustment composition to the fulvic acid solution to adjust the pH of the fulvic acid solution. In one aspect, the pH can be adjusted through the addition of water. The pH of the fulvic acid solution can be adjusted to a pH of about 1 to about 5. Thus, the fulvic acid solution used in the methods disclosed herein can have a pH of about 1.5 to about 4.

The fulvic acid compositions prepared by the above method can be dehydrated or freeze-dried to form a fulvic acid powder. The fulvic acid powder can be reconstituted with distilled water or another fulvic acid solution at a future date.

In another aspect of the present disclosure, natural materials can be preserved through the contacting of the natural material with a fulvic acid composition such as those disclosed herein. The preservation can act to preserve the structural and/or nutritional components of the natural material being preserved. The preservation can be accomplished utilizing similar methods disclosed herein for preparing an extract with the exception that the natural material is collected following its contacting with the fulvic acid composition, or by just mixing the fulvic and/or humic acid in with the product being preserved whether being a liquid, solid or vapor and whether or not being extracted by the fulvic acid composition. In some aspects, the natural material can be stored for extended periods of time while in contact with the fulvic acid compositions in order to facilitate preservation of the natural material.

In one aspect, dehydration may be used to increase the specific gravity of the extract solution. Dehydration may be accomplished using techniques readily known in the art, such as the use of a rotary evaporator. In one aspect, dehydration may be used to prepare the extract solution for storage. In one aspect, glycerin may be added after initiating dehydration to stabilize the dehydration process and protect the properties of the natural materials against degradation. In another aspect, glycerin may be added to the extract to stabilize the extract. In another aspect, the extract solution can be dehydrated to form a semi-solid solution that is less than 15% water by weight. In one aspect, the semi-solid solution may be encapsulated in gelatin tablets. In one aspect, the extract solution may be dehydrated or freeze dried.

EXAMPLES

Example 1—Extraction of Fulvic Acid From Humic Material

A fulvic acid solution that can be used in accordance with embodiments of the present disclosure is prepared in accordance to the following procedure. A large container (e.g. 55 gallon stainless steel drum or vat for human grade product or a plastic drum or vat for agriculture grade product) is filled with humic material. Water, such as distilled water, is poured over the top of the humic material and allowed to pass over and through the shale. Additional water is added daily and allowed to percolate over and through the shale. The effluent liquid collects in the bottom of the container and can be collected. The specific gravity of the effluent liquid is measured using a hydrometer (reference substance distilled water). If the desired specific gravity is not high enough, all or a portion of the effluent liquid can be re-poured over the humic material and allowed to percolate over and through the shale. In the event that the specific gravity of the effluent liquid is higher than desired, the effluent liquid can be diluted with water (e.g. distilled water). Typical desired specific gravity amounts can range from about 1 to about 100, although other values are also possible. Once the desired concentration of fulvic acid-containing solution is produced, the solution can be set aside for storage or use in any of the methods disclosed herein.

Example 2—Extraction of Fulvic Acid From Humic Shale

A fulvic acid solution that can be used in accordance with embodiments of the present disclosure is prepared in accordance to the following procedure. A large container (e.g. 55 gallon stainless steel drum) is filled with 300 pounds of humic shale that has been dried and cured for a period of 1-2 years. A gallon of water (e.g. distilled water) is poured over the top of the humic shale daily for a period of two weeks and allowed to pass over and through the shale. The effluent liquid collects in the bottom of the container and is collected. The specific gravity of the fluid is measured using a hydrometer (reference substance distilled water) and is determined to be about 70. The fulvic acid solution is collected and stored for future use. In one aspect the fulvic acid solution can be diluted to a lower specific gravity, e.g. 50, or 15.

Example 3—Extraction of Fulvic Acid From Lignite

A fulvic acid solution that can be used in accordance with embodiments of the present disclosure is prepared in accordance to the following procedure. A large container (e.g. 55 gallon stainless steel drum) is filled with 450 pounds of lignite. One to four (1-4) gallons of water (e.g. distilled water) is poured over the top of the lignite daily for a period of 10 days and allowed to pass over and through the shale. The effluent liquid collects in the bottom of the container and is collected. The specific gravity of the fluid is measured using a hydrometer (reference substance distilled water) and is determined to be about 50. The fulvic acid solution is collected and stored for future use.

Example 4—Preparation of Fulvic Acid Powder Concentrate

A fulvic acid powder concentrate can be produced from a fulvic acid-containing solution such as produced in Example 1. An amount of a fulvic acid-containing solution, such as produced in Example 1, can be placed in a low heat dehydrator until all or substantially all of the water is removed. The remaining powder material can be collected and stored for future use.

Example 5—Preparation of an Alfalfa Extract

An alfalfa extract is prepared utilizing a fulvic acid-containing solution, such as one prepared as described in Example 1. Eight (8) ounces of dried alfalfa is placed in a container for extracting. Several drops of fulvic acid-containing solution having a specific gravity of 70, such as prepared in Example 1, and 4-8 ounces of water. The alfalfa, water, and fulvic acid-containing solution are maintained in the container for a period of 90 minutes. The dried alfalfa is pressed, filtered and removed and the remaining Alfalfa Extract is collected and stored for future use.

Example 6—Preparation of an Acerola Cherry Extract

An acerola cherry extract is prepared utilizing a fulvic acid-containing solution, such as one prepared as described in Example 1. 10 pounds of fresh acerola cherries are placed in a large container for extracting. 5-10 gallons of fulvic acid-containing solution having a specific gravity of 5 to 20, such as prepared in Example 1, and a gallon of distilled water are added to the container. The acerola cherry, water, and fulvic acid-containing solution are maintained in the container for a period of 24 hours. The mixture is pressed and filtered and the acerola cherry extract is collected and stored for future use.

Example 7—Preparation of a Broccoli Extract

A broccoli extract is prepared utilizing a fulvic acid-containing solution, such as one prepared as described in Example 1. 1 pound of diced broccoli is placed in a container for extracting. 8 ounces of fulvic acid-containing solution having a specific gravity of 100, such as prepared in Example 1, and 10 cups of distilled water are added to the container. The broccoli, distilled water, and fulvic acid-containing solution are maintained in the container for a period of 3 days. The mixture can be pressed and then filtered and the broccoli extract is collected and stored for future use.

Example 8—Preparation of a Deer Antler Extract

A deer antler extract is prepared utilizing a fulvic acid-containing solution, such as one prepared as described in Example 1. 8 ounces of dried and ground deer antler is placed in a container for extracting. 1 ounce of fulvic acid-containing solution having a specific gravity of 70, such as prepared in Example 1, and one cup of distilled water are added to the container. The ground deer antler, distilled water, and fulvic acid-containing solution are maintained in the container for a period of 7 days with intermittent mixing. The mixture can be pressed and then filtered and the deer antler extract is collected and stored for future use.

Example 9—Preparation of a Beef Liver Extract

A beef liver extract is prepared utilizing a fulvic acid-containing solution, such as one prepared as described in Example 1. 2 pounds of dried and ground beef livers are placed in a container for extracting. 64 ounces of fulvic acid-containing solution having a specific gravity of 50, such as prepared in Example 1, and one cup of distilled water are added to the container. The dried and ground beef liver, distilled water, and fulvic acid-containing solution are maintained in the container for a period of 48 hours with intermittent mixing. The mixture can be pressed and then filtered and the beef liver extract is collected and stored for future use.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for producing a humic shale extract preparation, comprising:
    (a) drying an amount of humic shale for a period greater than one year;
    (b) contacting the amount of dried humic shale with a water extracted fulvic acid solution in a container for a predetermined period of time wherein said predetermined period of time ranges from 5 minutes to 24 hours;
    (c) mixing the amount of dried humic shale and water extracted fulvic acid solution after the amount of dried humic shale and water extracted fulvic acid solution have been in contact for the predetermined period of time;
    (d) after step (c), pressing the amount of dried humic shale and water extracted fulvic acid solution to create an effluent and a solid;
    (e) separating the effluent and the solid from the pressed amount of dried humic shale and water extracted fulvic acid solution;
    (f) after step (e), collecting the effluent and solid, wherein said effluent comprises a fulvic acid solution having a specific gravity greater than 2; and
    (g) after step (e), filtering the effluent.

2. The method of claim 1, further comprising collecting and pouring the effluent over the solids.

3. The method of claim 2, wherein the collecting and pouring of the effluent over the solids is repeated 2 times to 100 times.

4. The method of claim 2, wherein the collecting and pouring of the effluent over the solids is repeated 5 times to 50 times.

5. The method of claim 1, wherein the contacting includes submersing the humic shale in the fulvic acid solution.

6. The method of claim 5, wherein the humic shale is submersed in the fulvic acid solution for a period of 5 minutes to 14 days.

7. The method of claim 1, wherein the effluent comprises a fulvic acid solution having a specific gravity of at least 10.

8. The method of claim 1, wherein the effluent comprises a fulvic acid solution having a specific gravity of about 10 to about 100.

9. The method of claim 1, wherein the method is performed at room temperature.

10. The method of claim 1, wherein the method is performed without heating, without the addition of additional chemical agents, and without alcohol.

11. The method of claim 1, further comprising the step of adding glycerin to the effluent.

12. The method of claim 11, further comprising the steps of drying the effluent to form a powder.

13. The method of claim 12, wherein the dried effluent contains less than 15% water by weight.

14. The method of claim 1, further comprising adding distilled water to the effluent to adjust the specific gravity of the effluent.

15. The method of claim 14, wherein the period of time is about 24 hours to about 21 days.

16. The method of claim 14, wherein the period of time is about 36 hours to about 15 days.

17. The method of claim 14, wherein the period of time is about 5 days to about 14 days.

18. The method of claim 14, further comprising adding a pH adjustment composition to the effluent.

19. The method of claim 18, wherein the pH adjustment composition is water.

20. The method of claim 18, wherein the pH of the effluent has an adjusted pH of about 1 to about 4.

21. A method for producing a humic shale and lignite extract preparation, comprising:
    drying an amount of humic shale for a period greater than one year;
    contacting the amount of dried humic shale and an amount of lignite with a water extracted fulvic acid solution in a container for a predetermined period of time wherein said predetermined period of time ranges from 5 minutes to 2 days;
    mixing the amount of dried humic shale and water extracted fulvic acid solution after the amount of dried humic shale and water extracted fulvic acid solution have been in contact for the predetermined period of time;
    pressing the amount of dried humic shale and water extracted fulvic acid solution;
    separating an effluent from the pressed amount of dried humic shale and water extracted fulvic acid solution;
    separating solids from the pressed amount of dried humic shale and water extracted fulvic acid solution;
    collecting the effluent and solids, wherein the effluent comprises a fulvic acid solution having a specific gravity greater than 5 and the solids comprises humic shale and lignite.

22. The method of claim 21, further comprising (i) adding an amount of glycerin to the effluent and drying the effluent until it comprises less than 15% weight by water, and (ii) encapsulating the dried effluent for human consumption.

* * * * *